United States Patent

Stetsko et al.

[11] Patent Number: 5,340,589
[45] Date of Patent: * Aug. 23, 1994

[54] LOW SOLUBILITY DRUG-COATED BEAD COMPOSITIONS

[75] Inventors: Gregg Stetsko, Bethlehem, N.Y.; Kuei-Tu Chang, Mountain Lakes, N.J.

[73] Assignee: Sterling Winthrop Inc., New York, N.Y.

[*] Notice: The portion of the term of this patent subsequent to Jun. 29, 2010 has been disclaimed.

[21] Appl. No.: 60,326

[22] Filed: May 12, 1993

Related U.S. Application Data

[62] Division of Ser. No. 700,968, May 16, 1991, Pat. No. 5,223,268.

[51] Int. Cl.$^5$ ................................................ A61K 9/58
[52] U.S. Cl. ...................................... 424/462; 424/456
[58] Field of Search ................ 424/490, 489, 456, 462

[56] References Cited

U.S. PATENT DOCUMENTS

| | | | |
|---|---|---|---|
| 4,684,636 | 8/1987 | Christiansen et al. | 514/176 |
| 4,717,569 | 1/1988 | Harrison et al. | 424/494 |
| 5,223,268 | 6/1993 | Stetsko et al. | 424/490 |

FOREIGN PATENT DOCUMENTS

| | | |
|---|---|---|
| 0207375 | 6/1986 | European Pat. Off. |
| 0514967A1 | 5/1992 | European Pat. Off. |

*Primary Examiner*—Thurman K. Page
*Assistant Examiner*—William E. Benston, Jr.
*Attorney, Agent, or Firm*—Richard A. Hake; Paul E. Dupont; Theodore C. Miller

[57] ABSTRACT

Low solubility drug coated bead compositions, capsules filled therewith and method of preparation thereof, especially wherein the low solubility drug is an antiandrogenic steroid and most especially wherein the antiandrogenic steroid is (5α,17α)-1'-(methylsulfonyl)-1'-H-pregn-20-yno[3,2-c]pyrazol-17-ol, are disclosed.

6 Claims, No Drawings

LOW SOLUBILITY DRUG-COATED BEAD COMPOSITIONS

This invention is a division, of application Ser. No. 07/700,968, filed May 16, 1991 now U.S. Pat. No. 5,223,268.

BACKGROUND OF THE INVENTION

Field of the Invention

The invention relates to low solubility drug-coated bead compositions, capsules filled therewith and method of preparation thereof, especially wherein the low solubility drug is an antiandrogenic steroid and most especially wherein the antiandrogenic steroid is (5α,17α)-1'-(methylsulfonyl)-1'H-pregn-20-yno[3,2-c]pyrazol-17-ol.

Information Disclosure Statement

Harrison et al. U.S. Pat. No. 4,717,569 issued Jan.5, 1988 describes pharmaceutical compositions
for oral administration of a polycyclic medicament having a solubility in water and aqueous media at ambient temperatures of less than 1 part of the medicament in from 5,000 to greater than 10,000 parts by weight of the medium which comprises a plurality of beads, each bead comprising particles of finely divided solid medicament bound together by a binder soluble in water and aqueous media at all pH values normally found in the gastrointestinal tract, and preferably a pharmacologically acceptable wetting agent, said plurality of beads together constituting a unit dose. In a preferred embodiment, the unit dosage fore is enclosed in a gastric juice-soluble material, such as gelatin.

The beads can be "sugar/starch bead[s]". The compositions are described as having been prepared by coating the beads with an aqueous suspension of the medicament and binder and optional wetting agent and then encapsulated. Five examples are described wherein the medicament is "17a-pregna-2,4-diene-20-yno[2,3-d]isoxazol-17-ol( . . . Compound A)" and the binder is hydroxypropylmethylcellulose, one in which no wetting agent is included, four in which sodium lauryl sulphate is included as wetting agent, and three in which polyvinylpyrrolidone is included as a second binding agent. Improved human bioavailability of the medicament is shown by favorable comparison of several described formulations with corresponding conventional starch-lactose-talc-magnesium stearate dry powder capsule formulations.

Christiansen et al. U.S. Pat. No. 4,684,636 issued Aug. 4, 1987 describes antiandrogenic sulfonyl-steroidopyrazoles including (5α,17α)-1'-(methylsulfonyl)-1'-H-pregn-20-yno[3,2-c]pyrazol-17-ol as the product of EXAMPLE 1 and pharmaceutical compositions thereof in general including those
for oral . . . administration . . . in solid dosage form including capsules, tablets . . . Conventional pharmaceutically acceptable vehicles and techniques are used in preparing these dosage forms.
The patent does not describe any such composition specifically.

SUMMARY OF THE INVENTION

In a first composition of matter aspect the invention is sugar or sugar/starch beads coated with from about 10% to about 300% by weight of a coating composition consisting essentially of from about 1% to about 80% by weight of a drug having a solubility of less than 1% by weight in water and from about 1% to about 30% by weight each of a cellulose derivative selected from the group consisting of hydroxypropyl cellulose and hydroxypropyl methylcellulose, a polyethylene glycol or derivative thereof selected from the group consisting of a polyethylene glycol having a molecular weight from about 1,000 to about 8,000 and d-alpha tocopheryl polyethylene glycol 1000 succinate whose polyethylene glycol part has an average formula weight of about 1,000, and a waxy solid selected from the group consisting of the polyoxyethylene-polyoxypropylene-polyoxyethylene block copolymer having the structural formula

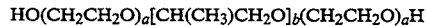

Formula I wherein a has a value of about 79 and b has a value of about 28, sulfobutanedioic acid 1,4-bis(2-ethylhexyl) ester sodium salt, and sulfuric acid monododecyl ester sodium salt.

A preferred composition of matter aspect of the invention is the first composition of matter aspect of the invention wherein the cellulose derivative is hydroxypropyl methylcellulose, the polyethylene glycol or derivative thereof is a polyethylene glycol having a molecular weight from about 1,000 to about 8,000 and the waxy solid is the polyoxyethylene-polyoxypropylene-polyoxyethylene block copolymer of Formula I wherein a has a value of about 79 and b has a value of about 28.

In a second composition of matter aspect the invention is a pharmaceutical capsule filled with from about 40 milligrams to about 700 milligrams of the first composition of matter aspect of the invention.

Preferably the composition of matter aspects of the invention are prepared for oral administration.

In a process aspect the invention is the process of preparing the first composition of matter aspect of the invention which comprises dissolving the cellulose derivative, the polyethylene glycol or derivative thereof and the waxy solid in from about three to about ten times their combined weight of water with warming, then suspending the drug in the resulting solution with agitation, then coating the beads with the resulting suspension, then drying the resulting coated beads.

DETAILED DESCRIPTION OF THE INVENTION INCLUSIVE OF THE PREFERRED EMBODIMENTS

The low solubility drug can be any drug having a solubility of less than 1% by weight in water and is especially asteroid and more particularly an androgenic, antiandrogenic, estrogenic, antiestrogenic, progestational, antiprogestational or cortical steroid including even more particularly a fertility regulant including contraceptive, metabolism regulant including anabolic, antiinflammatory, antiendometriosis, antiprostatohyperplasia or antiprostatocarcinoma steroid or any steroid having any combination of these properties. The antiandrogenic sulfonylsteroidopyrazoles of above-cited Christiansen et al. U.S. Pat. No.4,684,636 including especially (5α,17α)-1'-(methylsulfonyl)-1'-H-pregn-20-yno[3,2-c]pyrazol-17-ol and especially for treatment of benign prostatic hyperplasia and prostatic carcinoma are preferred. The preferred amount of drug is from about 40% to about 80% by weight of the coating composition.

The other substances used to prepare the first composition of matter aspect of the invention are known pharmaceutical or food ingredients and those except α-d-tocopheryl polyethylene glycol succinate whose polyethylene glycol part has an average formula weight of about 1,000 used to prepare the below-described examples are described by The United States Pharmacopeia, Twenty-second Revision and The National Formulary, Seventeenth Edition (a single volume also entitled 1990 USP XXII NF XVII; copyright by United States Pharmacopeial Convention, Inc., 12601 Twinbrook Parkway, Rockville, Md. 20852, 1989). A set of monographs is presented and arranged alphabetically by name in each of the United States Pharmacopeia (USP) and National Formulary (NF) sections thereof. The convention followed thereby in naming the substances described is that the first letter of each word of the name is capitalized. The substances used to prepare the first composition of matter aspect of the invention are described under the following names (section, page(s)): Docusate Sodium (USP, p. 471), Hydroxypropyl Methylcellulose (USP, pp. 670-671), Purified Water (USP, p. 1457), Hydroxypropyl Cellulose (NF, p. 1938), Poloxamer (NF, pp. 1960-1961), Polyethylene Glycol (NF, pp. 1961-1963), Sodium Lauryl Sulfate (NF, pp. 1980-1981), Sugar Spheres (NF, p. 1989).

Docusate Sodium is described as "[b]utanedioic acid, sulfo-, 1,4-bis(2-ethylhexyl) ester, sodium salt" and "[s]odium 1,4-bis(2-ethylhexyl) sulfosuccinate" containing "not less than 99.0 percent and not more than 100.5 percent of $C_{20}H_{37}NaO_7S$, calculated on the anhydrous basis."

Hydroxypropyl Methylcellulose is described as "[c]ellulose, 2-hydroxypropyl methyl ether" and as "a propylene glycol ether of methylcellulose", which "[w]hen dried at 105° C. for 2 hours . . . contains methoxy ($OCH_3$) and hydroxypropoxy ($OCH_2$-$CHOHCH_3$) groups" conforming to certain limits. Hydroxypropyl Methylcellulose 2910 is the preferred hydroxypropyl methylcellulose of the invention and has a minimum of 28.0% and a maximum of 30.0% of methoxy groups and a minimum of 7.0% and a maximum of 12.0% of hydroxypropoxy groups. Specifications are set forth for three other variants, which are designated by the numbers 1828, 2208 and 2906.

Purified Water is described as "obtained by distillation, ion-exchange treatment, reverse osmosis, or other suitable process" and as "prepared from water complying with the regulations of the federal Environmental Protection Agency with respect to drinking water" and "contains no added substance."

Hydroxypropyl Cellulose is described as "[c]ellulose, 2-hydroxypropyl ether" and as
 a partially substituted poly(hydroxypropyl) ether of cellulose. It may contain not more than 0.60 percent of silica, or other suitable anticaking agents. When dried at 105° for 3 hours, it contains not more than 80.5 percent of hydroxypropoxy groups. Poloxamer is described as "a synthetic block copolymer of ethylene oxide and propylene oxide" having the structural formula

wherein a and b have the following values corresponding to five variants:

| Poloxamer | a | b |
| --- | --- | --- |
| 124 | 12 | 20 |
| 188 | 79 | 28 |
| 237 | 64 | 37 |
| 338 | 141 | 44 |
| 407 | 101 | 56 |

The polyoxyethylene-polyoxypropylene-polyoxyethylene block copolymer of Formula I of the invention is Poloxamer 188, which is further described as being a solid and having an average molecular weight from 7680 to 9510.

Polyethylene Glycol is described as "an addition polymer of ethylene oxide and water, represented by the formula

in which n represents the average number of oxyethylene groups." The variants are designated by "nominal value" of "average molecular weight", which is explained as follows:
 The average molecular weight is not less than 95.0 percent and not more than 105.0 percent of the labeled nominal value if the labeled nominal value is below 1000; it is not less than 90.0 percent and not more than 110.0 percent of the labeled nominal value if the labeled nominal value is between 1000 and 7000; it is not less than 87.5 percent and not more than 112.5 percent of the
labeled nominal value if the labeled nominal value is above 7000.
Polyethylene glycols having nominal average molecular weights in the range from 300 to 8000 are described. Polyethylene Glycol 3350 is the preferred polyethylene glycol of the invention.

Sodium Lauryl Sulfate is also named as "[s]ulfuric acid monododecyl ester sodium salt" and "[s]odium monododecyl sulfate" and is described as
 a mixture of sodium alkyl sulfates consisting chiefly of sodium lauryl sulfate [$CH_3(CH_2)_{10}CH_2OSO_3Na$]. The combined content of sodium chloride and sodium sulfate is not more than 8.0 percent. d-Alpha tocopheryl polyethylene glycol 1000 succinate is described by
the manufacturer (Eastman Chemical Products, Inc., a division of Eastman Kodak Company, Kingsport, Tenn. 37662) in a product brochure dated Feb. 4, 1983 as "prepared from crystalline d-Alpha Tocopheryl Acid Succinate NF by esterification of the acid group with polyethylene glycol 1000", as also being named "Vitamin E TPGS", as being a "[p]ale yellow, waxy solid" having a specific gravity at 45° C. of approximately 1.06 and a melting point of approximately 40° C., and in the opinion of the manufacturer as being "recognized as safe ("GRAS") when used as an oral dietary supplement of vitamin E."

The preferred amount of each of the cellulose derivative, polyethylene glycol or derivative thereof and waxy solid in the first composition of matter aspect of the invention is from about 5% to about 30% by weight of the coating composition.

The preferred amount of each of the hydropropyl methylcellulose, polyethylene glycol and polyoxyethylene-polyoxypropylene-polyoxyethylene block copolymer in the preferred first composition of matter aspect of the invention is from about 5% to about 15% by weight of the coating composition.

Sugar Spheres are described as containing "not less than 62.5 percent and not more than 91.5 percent of sucrose ($C_{12}H_{22}O_{11}$), calculated on the dried basis, the remainder consisting chiefly of starch" and as consisting of "approximately spherical particles of a labeled nominal size range" and correspond to the sugar or sugar/starch beads of the invention. They can also be or be referred to as granules, particles, pellets or nonpareils and are from about 2 millimeters or about 10 mesh to about 0.2 millimeter or about 80 mesh, preferably from about 20 mesh to about 70 mesh, in diameter or longest dimension before coating. After coating the preferred diameter or longest dimension is from about 16 mesh to about 60 mesh.

The capsule shell of the second composition of matter aspect of the invention can be any pharmaceutically acceptable capsule shell but is preferably a gelatin capsule shell and can be a soft gelatin capsule shell or a hard gelatin capsule shell but is preferably a hard gelatin capsule shell and is of suitable size for containing from about 40 milligrams to about 700 milligrams of the first composition of matter aspect of the invention. Conventional machinery and technique are used in filling the capsule shells.

In the dissolution step of the process aspect of the invention the temperature of warming can be in the range from room temperature to about 100° C. and is preferably in the range from 50° C. to 60° C. About 80% of the total amount of water needed is used for the dissolution and suspension steps and the remainder is used for rinsing the last amounts of solution and suspension from the equipment. Preferably the polyethylene glycol or derivative thereof and the waxy solid are dissolved first, and the cellulose derivative is then added and dissolved. The low solubility drug is added to the resulting solution with agitation to form a suspension. The dissolution and suspension steps are carded out with conventional mixing equipment. The suspension is preferably passed through a colloid mill before carrying out the coating step and agitation is maintained during the coating step. The coating and drying steps are preferably carded out in a fluid bed processor with inlet air temperature in the range from 50° C. to 70° C. with preheating of the sugar or sugar/starch beads. After drying the coated beads are sifted to produce coated beads of the desired particle size, preferably 16–60 mesh.

The following composition in accordance with the first composition of matter aspect of the invention was prepared using the process aspect of the invention.

EXAMPLE 1

| Ingredient | Amount (kg.) |
|---|---|
| (5α,17α)-1'-(Methylsulfonyl)-1'H-pregn-20-yno[3,2-c]pyrazol-17-ol | 0.720 |
| Poloxamer 188, NF | 0.0900 |
| Polyethylene Glycol 3350, NF | 0.144 |
| Hydroxypropyl Methylcellulose, USP | 0.100 |
| Sugar Spheres (30–35 mesh), NF | 0.450 |
| Purified Water, USP (removed during processing) | 2.46 |
| Total amount of dry ingredients | 1.500 |

A portion of this composition sufficient to provide 200 mg. of the steroid drug when filled into a hard gelatin capsule has the following composition:

| Ingredient | Mg./Capsule |
|---|---|
| (5α,17α)-1'-(Methylsulfonyl)-1'H-pregn-20-yno[3,2-c]pyrazol-17-ol | 200. |
| Poloxamer 188, NF | 25.0 |
| Polyethylene Glycol 3350, NF | 40.0 |
| Hydroxypropyl Methylcellulose, USP | 27.8 |
| Sugar Spheres (30–35 mesh), NF | 125. |
| Total Capsule Fill Weight | 418. |

The amount of drug in each capsule can be varied by varying the capsule fill weight, the amount of drug in the coating composition or the amount of coating composition coated onto the sugar or sugar/starch beads.

The composition of Example 1 was shown to have improved bioavailability over a conventional tablet composition of the same drug when compared in the dog. The following conventional tablet composition was prepared using a conventional tablet preparation method.

Comparative Example

| Ingredient | Mg./Tablet |
|---|---|
| (5α,17α)-1'-(Methylsulfonyl)-1'H-pregn-20-yno[3,2-c]pyrazol-17-ol | 50.0 |
| Microcrystalline Cellulose, NF (Avicel pH 101) | 60.0 |
| Poloxamer 188, NF (Pluronic F68) | 6.0 |
| Lactose, NF (Spray Dry) | 161.5 |
| Croscarmellose Sodium, NF (Ac-Di-Sol) | 15.0 |
| Magnesium Stearate, NF | 1.5 |
| Povidone, USP (PVP, K29–32) | 6.0 |
| Total | 300.0 |

In separate but comparable experiments a single fifty-milligram dose of (5α,17α)-1'-(methylsulfonyl)-1'-H-pregn-20-yno[3,2-c]pyrazol-17-ol was administered orally in the form of the dried sugar coated spheres of Example 1 to each of ten dogs and in the form of the tablet of the Comparative Example to each of four dogs. Blood samples were taken at 0.25(tablet only), 0.5, 1, 2, 4, 6, 8, 10, 12 and 24 hours postmedication. The plasma concentration of (5α,17α)-1'-(methylsulfonyl)-1'-H-pregn-20-yno[3,2-c]pyrazol-17-ol was measured from each sample. The data were analyzed to determine the mean maximum concentration of (5α,17α)-1'-(methylsulfonyl)-1'-H-pregn-20-yno[3,2-c]pyrazol-17-ol reached (mean $C_{max}$) and the mean area under the (5α,17α)-1'-(methylsulfonyl)-1'H-pregn-20-yno[3,2-c]pyrazol-17-ol concentration-time curve for the twenty-four hour period (mean $AUC_{0-24}$). The following results were obtained and show greater bioavailability of the composition of Example 1.

| Composition | Mean $C_{max}$ (μg./ml.)(s.d.) | Mean $AUC_{0-24}$ (μg.-hr./ml.)(s.d.) |
|---|---|---|
| Comparative Example | 0.23 (0.11) | 1.70 (1.64) |
| Example 1 | 0.40 (0.08) | 3.4 (1.3) |

We claim:

1. A pharmaceutical capsule filled with from about 40 milligrams to about 700 milligrams of coated sugar or sugar/starch beads coated with from about 10% to about 300% by weight of a coating composition consisting essentially of from about 1% to about 80% by weight of a drug having a solubility of less than 1% by weight in water and from about 1% to about 30% by weight each of a cellulose derivative selected from the group consisting of hydroxypropyl cellulose and hydroxypropyl methylcellulose, a polyethylene glycol or derivative thereof selected from the group consisting of a polyethylene glycol having a molecular weight from about 1,000 to about 8,000 and d-alpha tocopheryl polyethylene glycol 1000 succinate whose polyethylene glycol part has an average formula weight of about 1,000, and a waxy solid selected from the group consisting of the polyoxyethylene-polyoxypropylene-polyoxyethylene block copolymer having the structural formula

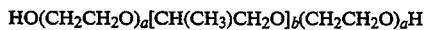

Formula I wherein a has a value of about 79 and b has a value of about 28, sulfobutanedioic acid 1,4-bis(2-ethylhexyl) ester sodium salt, and sulfuric acid monododecyl ester sodium salt.

2. A pharmaceutical capsule according to claim 1 prepared for oral administration.

3. A pharmaceutical capsule filled with from about 40 milligrams to about 700 milligrams of coated sugar or sugar/starch beads according to claim 1, wherein the coating composition consists essentially of from about 1% to about 80% by weight of a drug having a solubility of less than 1% by weight in water and from about 1% to about 30% by weight each of hydroxypropyl methylcellulose, a polyethylene glycol having a molecular weight from about 1,000 to about 8,000 and the polyoxyethylene-polyoxypropylene-polyoxyethylene block copolymer of Formula I.

4. A pharmaceutical capsule according to claim 3 prepared for oral administration.

5. A pharmaceutical capsule filled with from about 40 milligrams to about 700 milligrams of coated sugar or sugar/starch beads according to claim 3, wherein the coating composition consists essentially of hydropropyl methylcellulose, polyethylene glycol having a molecular weight of about 3350 and the polyoxyethylene-polyoxypropylene-polyoxyethylene block copolymer present in an amount from about 5% to about 15% by weight of the coating composition, and the drug is (5α,17α)-1'-(methylsulfonyl)-1'H-pregn-20-yno[3,2-c]pyrazol-17-ol, present in an amount from about 40% to about 80% by weight of the coating composition.

6. A pharmaceutical capsule according to claim 5 prepared for oral administration.

* * * * *